United States Patent
Arve

Patent Number: 5,705,166
Date of Patent: Jan. 6, 1998

[54] EXFOLIATING SKIN CREAM

[76] Inventor: Richard Arve, 2656 South A1A, Flagler Beach, Fla. 32136

[21] Appl. No.: 421,468

[22] Filed: Apr. 12, 1995

Related U.S. Application Data

[63] Continuation of Ser. No. 109,308, Aug. 18, 1993, abandoned, which is a continuation of Ser. No. 902,259, Jun. 22, 1992, abandoned, which is a continuation-in-part of Ser. No. 670,873, Mar. 18, 1991, abandoned.

[51] Int. Cl.⁶ .............................. A61K 6/00; A61K 7/00
[52] U.S. Cl. .............................. 424/401; 424/78.03
[58] Field of Search ........................ 424/401, 78.03

[56] References Cited

U.S. PATENT DOCUMENTS

| | | | |
|---|---|---|---|
| 4,062,937 | 12/1977 | Rea | 424/47 |
| 5,073,454 | 12/1991 | Arima et al. | 514/27 |
| 5,314,873 | 5/1994 | Tomila et al. | 514/21 |

*Primary Examiner*—Joseph L. Schofer
*Assistant Examiner*—William E. Benston, Jr.
*Attorney, Agent, or Firm*—Parsons & Goltry; Robert A. Parsons; Mike W. Goltry

[57] ABSTRACT

A defoliating enzyme mixed with a soothing ingredient and concentrated to form a cream for topical application to skin tissue which is activated by an activating pH level.

20 Claims, No Drawings

EXFOLIATING SKIN CREAM

CROSS-REFERENCE TO RELATED APPLICATION

This application is a continuation application of Ser. No. 08/109,308, filed 18 Aug. 1993, abandoned 12 Apr. 1995, which is a continuation application of Ser. No. 07/902,259, filed 22 Jun. 1992, abandoned 20 Aug. 1993, which is a continuation-in-part application of Ser. No. 07/670,873, filed 18 Mar. 1991, abandoned 7 Dec. 1991.

BACKGROUND OF THE INVENTION

1. Field of the Invention

This invention relates to skin care products.

More particularly, the present invention relates to creams which are used to exfoliate the skin.

2. Prior Art

Skin care has long been important to many people. This is especially true of facial skin care. Creams, lotions and cleansers are continually being developed in an attempt to supply a product which provides fresher healthier softer skin. Cleansers which clean the skin, moisturizers which soften, and exfoliators which attempt to remove dead skin cells are all used to try to reach this goal.

Cleansers are used to remove skin oils, dirt and other foreign material from the skin. Soap one of the earliest cleansers is quite successful in removing foreign material and oils from the skin. However, soap also tends to dry the skin. There have been many attempts to rectify this problem by adding moisturizers to soap in an attempt to keep skin soft and supple. Many additives to soap products clog skin pores resulting in various problems. After a cleanser is used, a moisturizer is often used in an attempt to soften and condition the skin. While moisturizers can condition dead skin cells, they cannot restore them or improve growth of new skin below the dead skin layers.

Often, an exfoliator is used in an attempt to remove dead skin cells exposing the living layers. This provides a smoother softer more youthful appearance, as well as allowing the living layers to grow and stay healthy. At the present time, exfoliating creams use an abrasive compound in a scrubbing motion to remove dead skin cells from the face. An example of an exfoliating cream is a cream containing apricot seeds. While these exfoliating creams are successful in removing dead skin cells, they may also remove living skin cells. These abrasive exfoliants can break small capillaries within the skin causing extreme irritation, often actually scratching the facial skin. Any benefits derived from exfoliating skin, may be negated by this extreme method of exfoliation.

It would be highly advantageous, therefore, to remedy the foregoing and other deficiencies inherent in the prior art.

Accordingly, it is an object of the present invention to provide a new and improved exfoliating cream.

Another object of the present invention is to provide an exfoliating cream which is not abrasive to the skin.

And another object of the present invention is to provide an exfoliating cream which selectively removes dead skin cells.

Still another object of the present invention is to provide an exfoliating cream which does not irritate the skin.

Yet another object of the present invention is to provide an exfoliating cream which may be used to help break up crosslink cells.

Yet still another object of the present invention is to provide a skin cream which will promote the growth of new skin layers.

SUMMARY OF THE INVENTION

Briefly, to achieve the desired objects of the instant invention in accordance with a preferred embodiment thereof, provided is a concentrated mixture of an exfoliating enzyme and a soothing and binding ingredient.

A method of producing an exfoliating cream wherein an exfoliating enzyme is mixed with a binding and soothing ingredient. This mixture is then concentrated into cakes by using an evaporating machine at a temperature not exceeding 110° F.

DETAILED DESCRIPTION OF THE PREFERRED EMBODIMENT

The present invention is directed to a novel exfoliating composition for topical application to skin tissue. The composition includes a combination of an exfoliating enzyme mixed with a binding and soothing ingredient. A pH modifier may also be used to maintain a desired pH value for the composition.

The preferred exfoliating enzyme is the proteolytic enzyme papain. Papain makes an excellent exfoliant, and may be found in unripened papaya in high concentrations. Papain becomes active at a relatively neutral pH, and is increasingly inactive as the pH is raised or lowered. The enzyme, when active, selectively dissolves dead skin cells. However, when active, the enzyme will also very quickly degrade and become ineffective. Furthermore, pure papain cannot be used in the composition because of the unique characteristics of this enzyme. Papain is encased in a protein coating, and when isolated from its natural state, will self-activate, becoming ineffective within hours.

Papain is activated over a specific range of pH values or activation pH. The activation pH is a gradient in the neutral range, but for purposes of this invention is substantially the same as the pH of normal human facial skin. The pH range of healthy facial skin is approximately 5.5–6.5. It has been found that a pH lower or higher than the activation pH prevents or reduces, depending upon how low or high a value is used, the activity of the enzyme, reducing degradation, and increasing the shelf life of the skin cream. The shelf life will depend upon how much inactivity is included in the enzyme.

In the preferred embodiment a very low, or acidic pH value is achieved by obtaining the enzyme papain from unripened papaya. Unripened papaya is rich in papain, and has a natural pH value of 4.0. Only unripened or green papaya can be used, because at the first stages of ripening the pH level of the fruit increases causing the degradation of the useful enzyme. The enzyme is rapidly degraded when the fruit starts ripening, and is not present in ripened fruit.

Therefore, in the preferred embodiment, an extract of unripened papaya is used, because it contains a high concentration of papain and helps preserve the enzyme by keeping it inactive. The extract is very acidic, having a pH value of approximately 4.0 thereby keeping the enzyme inactive. Since the extract is so acidic, it may cause burns on skin. A pH modifier must be used to increase the pH to a tolerable level. In the preferred embodiment, baking soda is used to raise the pH value to approximately 4.6. This is high enough to prevent burns, while acidic enough to keep the enzyme relatively inactive. It will be understood that while an acidic composition is used to keep the enzyme inactive, an alkaline composition may also be employed. However, since the natural papaya extract is acidic, a low pH is preferred.

The soothing ingredient used in the preferred embodiment, is raw honey. Besides being a natural moisturizer for skin, raw honey soothes the irritating effect of the enzyme on skin. While many sugar compounds have this soothing affect, honey has the best effect when used in combination with papain, and provides the best binder for forming the concentrated composition into cakes.

When a mixture of extract from unripened papaya and raw honey has been prepared, it is concentrated in an evaporating machine. It is important that the temperature in the evaporating machine does not exceed 110° F. A temperature which exceeds this level, will rapidly degrade the enzyme. The process of preparing the exfoliating cream, begins with obtaining the papaya extract. Only entirely green or unripened papayas are used, with no evidence of ripeness. The green papayas are cleaned and deseeded before being pressed in a pressing device which extracts substantially all the juice, leaving a fine residue of pulp. The papaya extract, also referred to as unripened papaya juice, is mixed with raw honey and placed in the evaporating machine. The preferred proportions of the composition is five parts papaya extract to one part raw honey. The composition is thoroughly mixed, and placed in the evaporating machine. This produces a concentrated material which can be formed into bricks or cakes.

As mentioned earlier, a pH modifier may also be added to the composition to obtain a desired pH. An example of a preferred composition forming the exfoliating face cream includes five gallons of pulpy concentrate mixed with one gallon of raw honey. The pH is increased by the addition of ¾ cup of baking soda. This combination is thoroughly mixed and placed in an evaporating machine which concentrates the mixture to between 80–84 bricks.

In order to receive the benefits of the face cream, the pH of the cream must be raised to an activation pH. The activation pH is reached by applying the cream to a moistened face. The pH of moistened facial skin tissue has a pH higher than the skin cream, ranging from approximately 5.5–6.5. This higher pH value is sufficient to raise the pH of the face cream, thereby activating the enzyme.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A composition for topical application to skin tissue and for exfoliating skin tissue comprising:
   unripened papaya juice containing papain and other substances occurring naturally in unripened papaya;
   a soothing and binding ingredient; and
   said soothing and binding ingredient, and said unripened papaya juice are thoroughly mixed and are concentrated.

2. A composition as claimed in claim 1 wherein said soothing ingredient is honey.

3. A composition as claimed in claim 1 having a pH outside of an activation pH range.

4. A composition as claimed in claim 3 wherein said activation pH range is between 5.5–6.5.

5. A composition as claimed in claim 3 further comprising a pH modifier.

6. A composition as claimed in claim 5 wherein said pH modifier is baking soda.

7. A composition as claimed in claim 1, wherein the proportions of said composition being five parts unripened papaya juice to one part soothing and binding ingredient.

8. A method of producing an exfoliating skin cream comprising the steps of:
   providing unripened papaya juice containing papain and other substances occurring naturally in unripened papaya;
   providing a soothing and binding ingredient;
   forming a mixture by combining said unripened papaya juice with said soothing and binding ingredient; and
   concentrating said mixture.

9. A method as claimed in claim 8 wherein said step of providing unripened papaya juice containing papain and other substances occurring naturally in unripened papaya further comprises the steps of:
   providing unripened papaya; and
   pressing said unripened papaya to obtain unripened papaya juice.

10. A method as claimed in claim 8 wherein said step of providing a soothing ingredient includes providing honey.

11. A method as claimed in claim 10 wherein forming a mixture further includes the step of mixing five parts of unripened papaya juice to one part of honey.

12. A method as claimed in claim 8 further comprising the step of combining a pH modifier with said unripened papaya juice and said soothing and binding ingredient to maintain a pH outside an activation pH range.

13. A method as claimed in claim 8 wherein said step of concentrating the mixture includes evaporating moisture from the mixture at a temperature which does not exceed 110° F.

14. A method of exfoliating epidermal tissues comprising the steps of:
   providing an exfoliating composition including;
      unripened papaya juice containing papain and other substances occurring naturally in unripened papaya,
      a soothing and binding ingredient, and
      a pH modifier maintaining a pH value of said composition outside of an activation range,
   moistening said epidermal tissue; and
   applying said composition to said moistened epidermal tissue.

15. A method as claimed in claim 14 wherein said step of applying, further includes the steps of activating said composition.

16. A method as claimed in claim 15 wherein the step of activating said composition includes the steps of:
   hydrating said composition with moisture from said moistened epidermal tissue; and
   altering said pH value of said composition to a value within said activation range.

17. A composition for topical application to skin tissue and for exfoliating skin tissue made by the following method, comprising the steps of:

providing unripened papaya juice containing papain and other substances occurring naturally in unripened papaya;

providing a soothing and binding ingredient;

forming a mixture by combining said unripened papaya juice with said soothing and binding ingredient; and concentrating said mixture.

18. A composition as claimed in claim 17 wherein said step of providing unripened papaya juice containing papain and other substances occurring naturally in unripened papaya further comprises the steps of:

providing unripened papaya; and pressing said unripened papaya to obtain unripened papaya juice containing papain and other substances occurring naturally in unripened papaya.

19. A composition as claimed in claim 18 wherein said step of providing a soothing ingredient includes providing honey.

20. A composition as claimed in claim 19 wherein forming a mixture further includes the step of mixing five parts of unripened papaya juice to one part of honey.

* * * * *